United States Patent [19]
Bandy

[11] Patent Number: 6,058,762
[45] Date of Patent: May 9, 2000

[54] SAMPLE PREPARATION UNIT

[76] Inventor: Mark S. Bandy, 1608 36th Ave. South, Fargo, N. Dak. 58104

[21] Appl. No.: 09/073,472

[22] Filed: May 6, 1998

[51] Int. Cl.[7] .............................. G01N 11/10; G01N 7/20
[52] U.S. Cl. ............................................. 73/54.23; 73/169
[58] Field of Search ................................ 73/53.01, 54.01, 73/54.16, 54.23, 54.28, 54.31, 54.43, 169

[56] References Cited

U.S. PATENT DOCUMENTS

| | | | |
|---|---|---|---|
| 4,235,965 | 11/1980 | Walon ...................................... | 435/174 |
| 4,879,897 | 11/1989 | Booth et al. ............................ | 73/54.31 |
| 5,003,814 | 4/1991 | Crawford et al. ...................... | 73/54.28 |

*Primary Examiner*—Daniel S. Larkin
*Assistant Examiner*—Jay L. Politzer
*Attorney, Agent, or Firm*—Zarley, McKee, Thomte Voorhees & Sease; Dennis L. Thomte

[57] ABSTRACT

The sprout damage testing apparatus of the present invention includes a housing with a mixing cup for receiving a grain sample therein. A first tank supplies a first reagent through a conduit to the mixing cup and a mixer mixes the first reagent and sample within the mixing cup. A drain tube drains the mixture from the mixing cup to a reactor vessel, where a heater warms the contents within the reactor vessel. A viscosity sensor includes a blade mounted within the reactor vessel to mix the contents of the vessel while measuring viscosity thereof. The sensor includes a transmitter for transmitting data relative to the viscosity of the mixture to a central control apparatus, for recording. A drain pipe extends from a drain in the vessel and includes a pump for placing a vacuum on the drain to exhaust the contents of the vessel. A second conduit extends from a second tank with a second reagent therein, which is dispensed within the reactor vessel to dissolve the mixture and enhance the drainage thereof. A third conduit extends from a third tank and sprays a third reagent into the vessel to clean the vessel. Operable valves are connected to the central control apparatus and are located in the various conduits and drain pipes and drain tubes to selectively dispense reagent and drain the sample cup and reactor vessel. The method for determining damage to grain of the present invention includes placing a weighed sample of grain into a mixing cup and thence adding a reagent to the sample and mixing the two components. Once the components are blended, they are transferred to a heated reactor vessel to activate enzyme activity in the grain. A viscosity sensor mixes the mixture while periodically determining the viscosity thereof and recording the viscosity. Once the mixture has reached the maximum viscosity, the viscosity is recorded and the contents of the reactor vessel are drained therefrom.

20 Claims, 4 Drawing Sheets

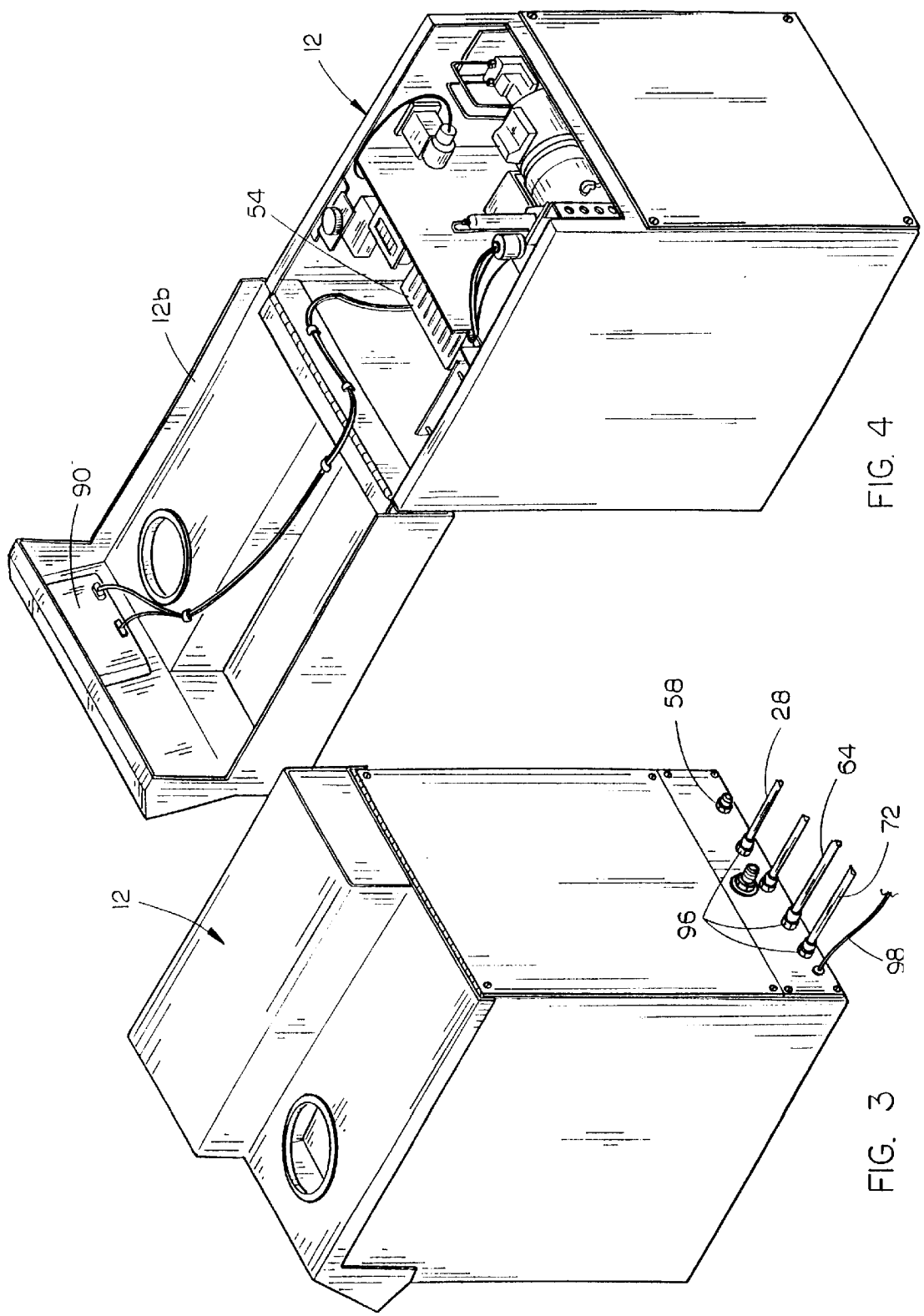

SAMPLE PREPARATION UNIT

TECHNICAL FIELD

The present invention relates generally to an apparatus and a method for measuring sprout damage in grain, and more particularly to an improved sample preparation unit and method which permits processing of whole grain samples and automates the procedure.

BACKGROUND OF THE INVENTION

Sprout damaged or other unsound grain can cause significant expense if permitted to be mixed with sound grain or when used in milled products. In both cases, corrective action must be taken to bring the grain or products within compliance of FDA requirements.

Sprout damage occurs during harvest as a result of rain or excess moisture. This moisture enhances the production of an enzyme in grain called alpha amylase. This enzyme reduces the bonding capability of the grain, which in turn reduces the viscosity. The lower the viscosity, the lower the quality of grain.

There are various prior art systems on the market which check for sprout damage. However, such systems suffer a number of problems. First, prior art systems typically require the use of laboratory personnel and require a large amount of manual testing procedures. The intensive use of personnel makes prior art systems quite expensive, and thus are only infrequently used to test for sprout damage.

SUMMARY OF THE INVENTION

It is therefore a general object of the present invention to provide an improved apparatus and method for determining sprout damage.

Another object is to provide an improved method and apparatus for determining sprout damage which does not require laboratory personnel to obtain quick and accurate results.

A further object of the present invention is to provide an improved apparatus and method for determining sprout damage which is substantially automatic and provides repeatable testing capabilities.

These and other objects of the present invention will be apparent to those skilled in the art.

The sprout damage testing apparatus of the present invention includes a housing with a mixing cup for receiving a grain sample therein. A first tank supplies a first reagent through a conduit to the mixing cup and a mixer mixes the first reagent and sample within the mixing cup. A drain tube drains the mixture from the mixing cup to a reactor vessel, where a heater warms the contents within the reactor vessel. A viscosity sensor includes a blade mounted within the reactor vessel to mix the contents of the vessel while measuring viscosity thereof. The sensor includes a transmitter for transmitting data relative to the viscosity of the mixture to a central control apparatus, for recording. A drain pipe extends from a drain in the vessel and includes a pump for placing a vacuum on the drain to exhaust the contents of the vessel. A second conduit extends from a second tank with a second reagent therein, which is dispensed within the reactor vessel to dissolve the mixture and enhance the drainage thereof. A third conduit extends from a third tank and sprays a third reagent into the vessel to clean the vessel. Operable valves are connected to the central control apparatus and are located in the various conduits and drain pipes and drain tubes to selectively dispense reagent and drain the sample cup and reactor vessel. The method for determining damage to grain of the present invention includes placing a weighed sample of grain into a mixing cup and thence adding a reagent to the sample and mixing the two components. Once the components are blended, they are transferred to a heated reactor vessel to activate enzyme activity in the grain. A viscosity sensor mixes the mixture while periodically determining the viscosity thereof and recording the viscosity. Once the mixture has reached the maximum viscosity, the viscosity is recorded and the contents of the reactor vessel are drained therefrom.

BRIEF DESCRIPTION OF THE DRAWINGS

FIG. 3 is a rearward perspective view of the sprout damage indicator; and

FIG. 4 is a perspective view of the invention with the cover pivoted upwardly to show the interior thereof.

DESCRIPTION OF THE PREFERRED EMBODIMENT

Figure 1:
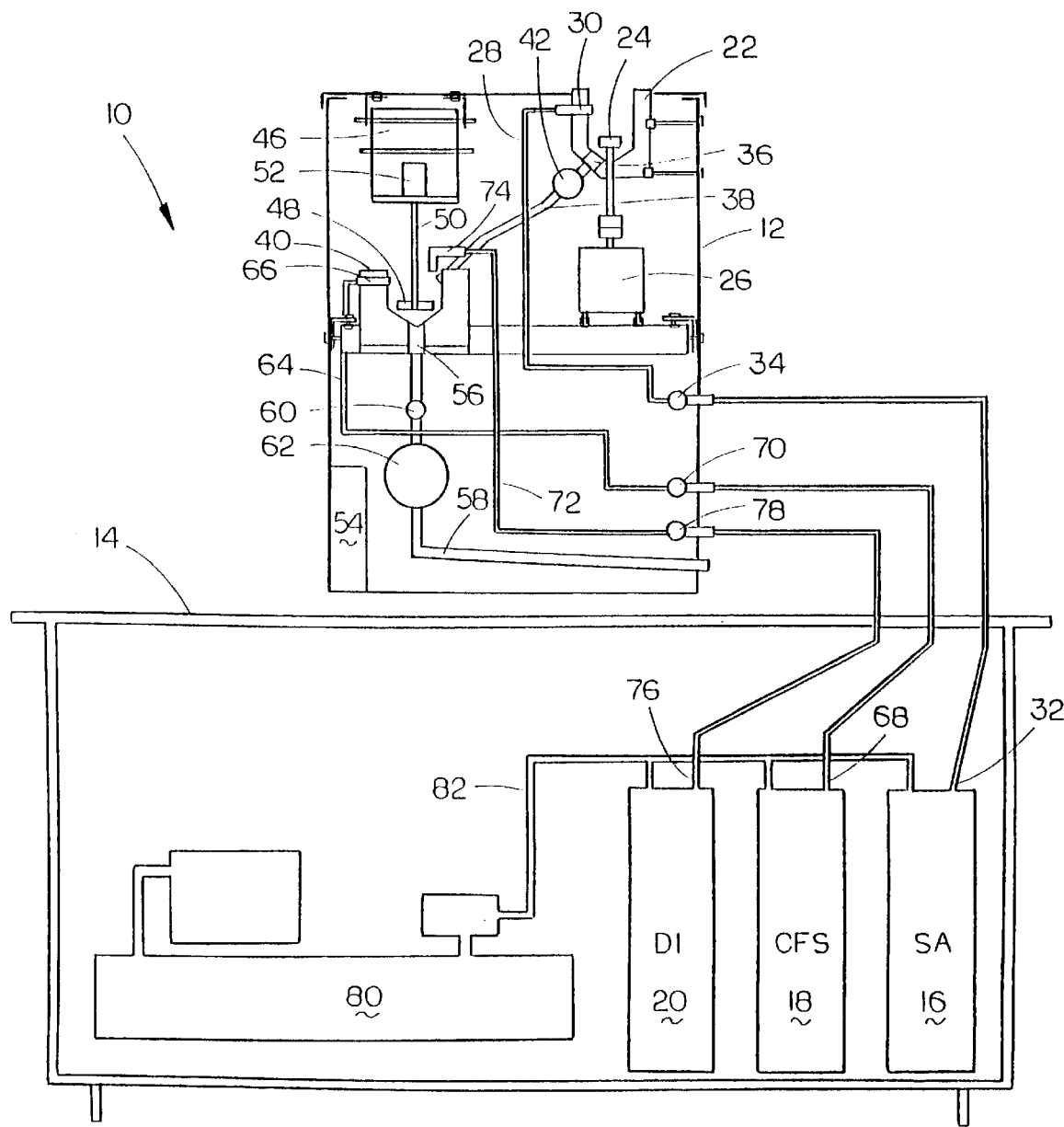
FIG. 1 is a schematic diagram of the sprout damage indicator of the present invention.

Referring now to FIG. 1, the sprout damage indicator of the present invention is designated generally at 10 and is shown in general schematic form. A housing 12 holds the processing equipment while a cabinet 14 stores three tanks 16, 18, and 20 which hold reagents therein for use during processing.

A sample cup 22 is located at the upper end of housing 12 and will receive a weighed sample of the grain which is to be tested. Sample cup 22 has the blade 24 of a mixer 26 operably mounted therein for rotation within the sample cup. A first conduit 28 has an outlet 30 connected to sample cup 22 to dispense a first reagent into the sample cup. The inlet end 32 of conduit 28 is connected to first tank 16 containing the first reagent therein. A control valve 34 is interposed in conduit 28 to selectively open and close, permitting the reagent to be dispensed within sample cup 22.

A drain 36 in the lower end of sample cup 22 is connected to a drain tube 38, which extends from sample cup 22 to a reactor vessel 40 within the housing 12. A valve 42 is provided in drain tube 38 to selectively open and close, and thereby selectively drain the contents of sample cup 22 to reactor vessel 40.

Reactor vessel 40 includes a heating unit 44 which will warm the vessel 40 to maintain the aqueous mixture within the vessel at the desired temperature. Preferably, reactor vessel 40 is a Teflon®-coated aluminum structure which is capable of maintaining product at a temperature of about 95° C. A viscometer 46 is mounted in housing 12 and includes a blade 48 on the end of a shaft 50 which will rotate within reactor vessel 40. Viscometer 46 provides two functions. First, blade 48 will mix the contents of reactor vessel 40. Second a sensor 52 is connected to shaft 50 and blade 48 to sense the viscosity of the aqueous mixture within reactor vessel 40. Sensor 52 periodically senses the viscosity, and transmits the data to a central control apparatus 54, for recording.

A drain 56 is provided in the lower end of reactor vessel 40 to drain the contents thereof through a drain pipe 58 and thence out of housing 12. A drain valve 60 is interposed in drain pipe 58 to selectively open and close, and thereby selectively drain the contents of reactor vessel 40. A drain pump 62 has also interposed in drain pipe 58 to create a vacuum and thereby create a more complete drainage of the reactor vessel.

A second conduit 64 is provided with an outlet 66 connected to the reactor vessel 40 to dispense a second reagent from second tank 18 into the reactor vessel. The inlet 68 of second conduit 64 is connected to second tank 18 within cabinet 14. A control valve 70 is interposed in second conduit 64 within housing 12 and is operable between open and closed positions to selectively permit the flow of the second reagent through second conduit 64.

A third conduit 72 has a spray nozzle 74 on an outlet end thereof, disposed over the upper end of reactor vessel 40, to spray a third reagent into the interior of reactor vessel 40. The inlet 76 on the opposite end of conduit 72 is connected to third tank 20 to communicate the third reagent therein to spray nozzle 74. A control valve 78 is interposed in third conduit 72 in housing 12 and is operable between open and closed positions to selectively permit the flow of the third reagent from third tank 20.

An air compressor 80 is provided within cabinet 14 and includes a pneumatic tube 82 extending therefrom and connected to first, second and third tanks 16, 18 and 20 to supply compressed air thereto. The compressed air pressurizes tanks 16, 18 and 20 to cause the reagents therein to travel through the associated conduits when the associated control valves are open.

It should be noted that mixer 26, control valves 34, 70 and 78, drain valves 42 and 60, heating unit 44, viscosity 46 and sensor 52 are all electrically operated and electrically connected to central control apparatus 54. Central control apparatus 54 preferably includes a computer for selectively operating all of these devices as required by the method of the invention, as described in more detail hereinbelow.

Figure 2:
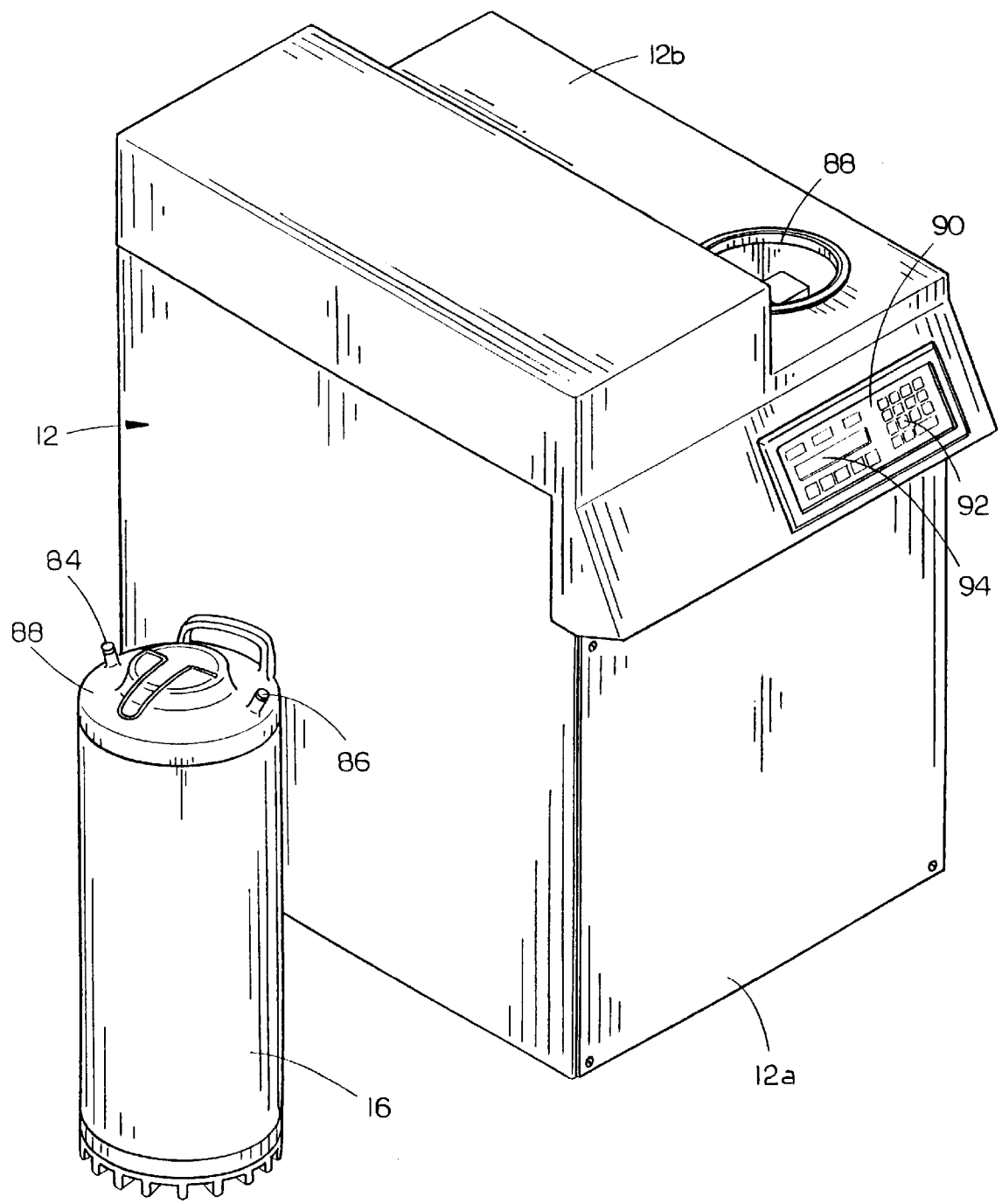
FIG. 2 is a perspective view of the sprout damage indicator with an example of one tank adjacent thereto.

Referring now to FIG. 2, housing 12 of the processing portion of the sprout damage indicator is shown adjacent one tank 16 from the cabinet 14. Tank 16 is preferably a canister which may be pressurized, having an inlet port 84 and outlet 86 on the upper end thereof. A lid 88 is removable to permit access to the interior of the tank, to replenish the reagent therein.

Housing 12 includes a base portion 12a and a lid portion 12b pivotally connected to the base portion 12a. An opening 88 in lid portion 12b permits access to the sample cup 22 (shown in FIG. 1). An operating panel 90 includes a keyboard 92 and data display 94, and is mounted to lid portion 12b. Operating panel 90 permits the programming of various parameters into the central control apparatus, and permits display of pertinent information on data display 94, from central control apparatus 54 (shown in FIG. 1).

Referring now to FIG. 3, the rearward side of housing 12 is displayed. First, second and third conduits 28, 64 and 72 enter the housing at connectors 96, in a conventional fashion. Drain pipe 58 is also shown exiting housing 12. A power cord 98 supplying power to the central control apparatus and all electrical devices is also shown entering housing 12 through the back thereof.

FIG. 4 is a perspective view of housing 12 with lid portion 12b pivoted to an open position to show the interior of housing 12. It can be seen that operating panel 90 is electrically connected to the central control apparatus 54, to transmit and receive data to and from central control apparatus 54.

Referring once again to FIG. 1, the method of the present invention includes the initial step of placing a weighed sample of the desired grain within sample cup 22. The grain may be a whole grain, a ground grain, or a milled flour sample. The sample may be provided to sample cup 22 by a human operator, or may easily incorporate automated sampling equipment, to provide samples from a stream of product at periodic intervals.

Once the sample has been placed within sample cup 22, control valve 34 is opened to dispense a quantity of a first reagent from first tank 16 into sample cup 22. Once a predetermined amount of reagent has been dispensed, control valve 34 will close and mixer 26 will be operated to rotate blade 24 and blend the sample and reagent into a mixture. Once the sample and reagent have been uniformly mixed, drain valve 42 is activated to drain the mixture from sample cup 22 and deposit it within reactor vessel 40. Additional reagent from the first conduit 28 may be utilized to assist in the transfer of the mixture through drain tube 38 to reactor vessel 40. Heater 44 maintains the interior of reactor vessel 40 at a predetermined temperature which enhances the reaction of the reagent and sample, to thereby encourage any enzyme activity. It has been found that a temperature of approximately 95° C. is preferred when reacting a wheat sample. Once the mixture has been deposited within reactor vessel 40, viscosity 46 is activated to simultaneously stir the mixture and measure its viscosity while the reaction is occurring. The reaction is permitted to continue for a predetermined period of time to ensure that the maximum viscosity is measured. Periodic viscosity readings are transmitted to the central control apparatus and electronically stored.

Once the test has been completed, a second reagent from second tank 18 is dispensed within reactor vessel 40. The second reagent is of a type which will dissolve the mixture within vessel 40, and is preferably mixed with the mixture for a period of time in order to initiate the dissolution process. Drain valve 60 is then activated along with drain pump 62 to drain the dissolved mixture under vacuum through drain pipe 58 and thence out of housing 12. Reactor vessel 40 is then cleaned by dispensing a third reagent from third tank 20 through spray nozzle 74 into reactor vessel 40. Spray nozzle 74 dispensing the third reagent under pressure to thoroughly clean the reactor vessel. This solution is then drained out of drain pipe 58. The system is then ready to test another sample.

Figure 5:
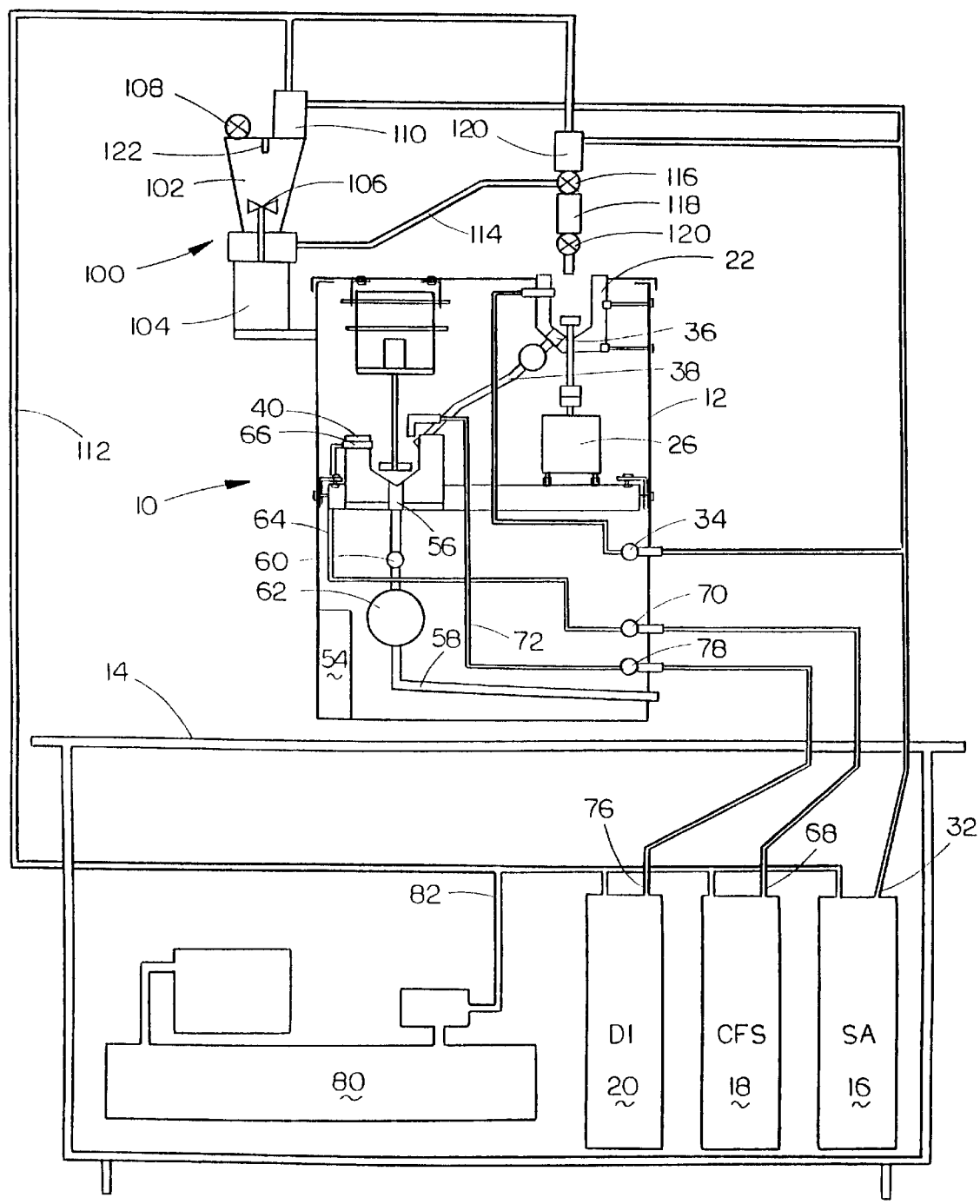
FIG. 5 is a schematic diagram of a wet grinding apparatus for preparing a sample for use in the sprout damage indicator.

Referring now to FIG. 5, a wet grinding apparatus is designated generally at 100, and is utilized to wet grind a whole grain from a stream of product. Wet grinding apparatus includes a grinder cup 102 mounted atop a motor 104 with a grinding blade 106, driven by motor 104, within grinding cup 102. A grain inlet valve 108 is operable to provide whole grain to grinding cup 102, as needed. A 180 ml fill container 110 has an air inlet connected to pneumatic line 112 and thence to air compressor 80 and a liquid inlet connected to the first reagent tank 16.

The slurry formed within grinder cup 102 is drained from grinder cup 102 and conveyed via tube 114 to an upper valve 116 at the upper end of a slurry lope 118. A second liquid container 120 is also connected to upper valve 116, with an air inlet connected to pneumatic line 112 and a liquid inlet connected to first reagent tank 16. A lower valve 120 in slurry loop 118 will drain the contents of slurry loop 118 into mixing cup 22 of the sprout damage indicator 10.

In operation, grain inlet valve 108 is opened and grain will enter grinder cup 102. Simultaneously, the liquid in tank valve on container 110 will open to permit a measured quantity of liquid from tank 16 to fill container 110. Second container 120 will also be filled with liquid reagent from first tank 16.

Once container 110 has been filled, the measured liquid will be emptied into grinder cup 102 while the measured liquid in container 120 is emptied, via slurry loop 118 into mixing cup 22.

Once grinder cup 102 has been filled with the appropriate amount of grain and liquid reagent, blade 106 is operated by motor 104 to wet grind the grain. After the grinding cycle has been concluded, grinder cup 102 is pressurized via pneumatic line 112 through container 110, and the slurry within grinder cup 102 is transferred through tube 114 and valve 116 to slurry loop 118. Slurry loop 118 is activated and lower valve 120 dumps the measured slurry into mixing cup 22. Container 120 is then operated for one cycle, and rinses the remaining slurry within slurry loop 118 into mixing cup 22. The regular operation of the sprout damage indicator 10 then occurs, as described hereinabove. A spray nozzle 122 in grinder cup 102 is then selectively operated to rinse and clean the grinder cup.

Whereas the invention has been shown and described in connection with the preferred embodiment thereof, many modifications, substitutions and additions may be made which are within the intended broad scope of the appended claims.

What is claimed is:

1. In combination:

A sample preparation unit and a sprout damage indicator, said sample preparation unit adapted to provide a grain slurry to said sprout damage indicator;

said sprout damage indicator including:
a mixing cup with a chamber drain in a lower end;
a first tank having a first reagent therein, connected via a first conduit to said mixing cup for selective dispensing of said first reagent into said mixing cup;
a first conduit valve in said first conduit, operable between open and closed positions;
a first mixer having a first blade located within said mixing cup, operable to mix contents within said mixing cup;
a drain tube extending from said chamber drain to a reactor vessel;
a drain tube valve in said drain tube, operable between open and closed positions;
a heater connected to said reactor vessel to warm contents within said reactor vessel;
a second mixer having a second blade located within said reactor vessel, operable to mix contents within said reactor vessel;
a drain pipe extending from a vessel drain in said reactor vessel, for draining contents of said reactor vessel;
a drain pipe valve in the drain pipe, operable between open and closed positions; and
apparatus for sensing viscosity, mounted proximal said reactor vessel with means located within said reactor vessel to sense viscosity of contents of said reactor vessel; and said sample preparation unit including:
a slurry loop arranged over said mixing cup and operable to selectively hold and dispense a grain slurry into said mixing cup;
said slurry loop being connected to a source of air pressure, said first tank, and a grinder cup, to selectively receive air pressure, said first reagent, and grain slurry, respectively;
said grinder cup having a grinder blade operable to wet grind grain and reagent therein, and further having a drain fluidly connected to said slurry loop to supply slurry to said slurry loop; and
said grinder cup connected to a source of grain, a source of air pressure, and said first tank, to selectively receive grain, air pressure and said first reagent, respectively.

2. The combination of claim 1, further comprising a central control apparatus connected to said first conduit valve, said drain tube valve, said drain pipe valve and said viscosity sensor, for selectively operating each of said first conduit valve, said drain tube valve and said viscosity sensor at predetermined intervals.

3. The combination of claim 2, wherein said viscosity sensor is connected to said second mixer and second blade, for sensing viscosity by movement of said second blade within said reactor vessel.

4. The combination of claim 3, further comprising:
recording apparatus for recording data transmitted from said viscosity sensor, said recording apparatus being connected to said central control apparatus and said viscosity sensor; and
wherein said viscosity sensor includes means for transmitting data regarding viscosity to said recording apparatus.

5. The combination of claim 4, further comprising a second conduit extending from said reactor vessel to a second tank containing a second reagent, and a second conduit valve operably mounted within said second conduit, operable between open and closed positions.

6. The combination of claim 5, wherein said second conduit valve is connected to said central control apparatus for selective operation by said central control apparatus.

7. The combination of claim 6, further comprising a drain pump interposed in said drain pipe downstream of said vessel drain, operable to create a vacuum within said pipe to pull contents of said reactor vessel through said drain pipe; said drain pump being connected to said central control apparatus for selective operation by said central control apparatus.

8. The combination of claim 7, further comprising a third conduit extending from said reactor vessel to a third tank containing a third reagent, and a third conduit valve mounted within said third conduit, operable between open and closed positions.

9. The combination of claim 8, wherein said third conduit valve is connected to said central control apparatus for selective operation by said central control apparatus.

10. The combination of claim 9, further comprising a spray nozzle connected to an outlet end of said third conduit and directed into said vessel, for spraying said reactor vessel with said third reagent.

11. The combination of claim 2, further comprising:
recording apparatus for recording data transmitted from said viscosity sensor, said recording apparatus being connected to said central control apparatus and said viscosity sensor; and
wherein said viscosity sensor includes means for transmitting data regarding viscosity to said recording apparatus.

12. The combination of claim 11, further comprising a second conduit extending from said reactor vessel to a second tank containing a second reagent, and a second conduit valve operably mounted within said second conduit, operable between open and closed positions.

13. The combination of claim 12, wherein said second conduit valve is connected to said central control apparatus for selective operation by said central control apparatus.

14. The combination of claim 13, further comprising a drain pump interposed in said drain pipe downstream of said vessel drain, operable to create a vacuum within said drain pipe to pull contents of said reactor vessel through the drain pipe; said drain pump being connected to said central control apparatus for selective operation by said central control apparatus.

15. The combination of claim 14, further comprising a third conduit extending from said reactor vessel to a third tank containing a third reagent, and a third conduit valve mounted within said third conduit, operable between open and closed positions.

16. The combination of claim 15, wherein said third conduit valve is connected to said central control apparatus for selective operation by saide central control apparatus.

17. The combination of claim 2, further comprising a second conduit extending from said reactor vessel to a second tank containing a second reagent, and a second conduit valve operably mounted within said second conduit, operable between open and closed positions.

18. The combination of claim 17, wherein said second conduit valve is connected to said central control apparatus for selective operation by said central control apparatus.

19. The combination of claim 18, further comprising a drain pump interposed in said drain pipe downstream of said vessel drain, operable to create a vacuum within said drain pipe to pull contents of said reactor vessel through said drain pipe; said drain pump being connected to said central control apparatus for selective operation by said central control apparatus.

20. The combination of claim 2, further comprising a drain pump interposed in said drain pipe downstream of said vessel drain, operable to create a vacuum within said drain pipe to pull contents of said reactor vessel through said drain pipe; said drain pump being connected to said central control apparatus for selective operation by said central control apparatus.

* * * * *